(12) United States Patent
Haj-Ahmad

(10) Patent No.: US 9,845,463 B2
(45) Date of Patent: Dec. 19, 2017

(54) METHODS AND COLUMNS FOR NUCLEIC ACID PURIFICATION

(71) Applicant: Norgen Biotek Corp., Thorold (CA)

(72) Inventor: Yousef Haj-Ahmad, St. Catharines (CA)

(73) Assignee: NORGEN BIOTEK CORP., Ontario (CA)

( * ) Notice: Subject to any disclaimer, the term of this patent is extended or adjusted under 35 U.S.C. 154(b) by 0 days.

(21) Appl. No.: 15/213,765

(22) Filed: Jul. 19, 2016

(65) Prior Publication Data

US 2016/0326512 A1   Nov. 10, 2016

Related U.S. Application Data

(62) Division of application No. 14/696,837, filed on Apr. 27, 2015, now Pat. No. 9,422,596.

(51) Int. Cl.
| | |
|---|---|
| *G01N 30/02* | (2006.01) |
| *G01N 30/60* | (2006.01) |
| *C12N 15/10* | (2006.01) |
| *C12Q 1/68* | (2006.01) |
| *C07H 21/04* | (2006.01) |
| *C07H 21/02* | (2006.01) |
| *C07H 1/06* | (2006.01) |
| *B01D 15/38* | (2006.01) |
| *C07H 1/08* | (2006.01) |

(52) U.S. Cl.
CPC ....... *C12N 15/101* (2013.01); *B01D 15/3804* (2013.01); *C07H 1/06* (2013.01); *C07H 21/02* (2013.01); *C07H 21/04* (2013.01); *C12N 15/1006* (2013.01); *C12N 15/1017* (2013.01); *C12Q 1/6806* (2013.01); *C07H 1/08* (2013.01)

(58) Field of Classification Search
CPC .............................. G01N 30/02; G01N 30/60
See application file for complete search history.

(56) References Cited

U.S. PATENT DOCUMENTS

| | | | |
|---|---|---|---|
| 5,075,430 A | 12/1991 | Little | |
| 5,155,018 A | 10/1992 | Gillespie | |
| 5,234,809 A | 8/1993 | Boom | |
| 5,342,931 A | 8/1994 | Woodard | |
| 5,629,186 A * | 5/1997 | Yasukawa | ............... A61L 27/10 428/325 |
| 5,808,041 A | 9/1998 | Padhye | |
| 6,027,945 A | 2/2000 | Smith | |
| 6,177,278 B1 | 1/2001 | Haj-Ahmad | |
| 6,218,531 B1 | 4/2001 | Ekenberg | |
| 6,291,248 B1 | 9/2001 | Haj-Ahmad | |
| 6,368,800 B1 | 4/2002 | Smith | |
| 6,566,145 B2 * | 5/2003 | Brewer | ................. B01L 3/0275 210/661 |
| 7,026,453 B2 | 4/2006 | Haj-Ahmad | |
| 7,329,491 B2 | 2/2008 | Kirchgesser | |

(Continued)

FOREIGN PATENT DOCUMENTS

CA   2517770   2/2007

*Primary Examiner* — Jan Ludlow
(74) *Attorney, Agent, or Firm* — Coats & Bennett, PLLC

(57) ABSTRACT

Provided are methods and columns employing a solid support comprising silica and silicon carbide for the isolation and purification of nucleic acids, and in particular, the isolation and purification of both high and low molecular weight RNA.

14 Claims, 5 Drawing Sheets

(56) References Cited

U.S. PATENT DOCUMENTS

| | | |
|---|---|---|
| 7,431,842 B2 | 10/2008 | Haj-Ahmad |
| 7,655,794 B2 | 2/2010 | Takkellapati |
| 7,893,228 B2 | 2/2011 | Heath |
| 7,989,614 B2 | 8/2011 | Deggerdal |
| 8,030,034 B2 | 10/2011 | Bitner |
| 8,063,199 B2 | 11/2011 | Haj-Ahmad |
| 8,067,579 B2 | 11/2011 | Skagestad |
| 8,202,693 B2 | 6/2012 | Guo |
| 2006/0270843 A1* | 11/2006 | Hall .................. C12N 15/1006 536/25.4 |
| 2010/0278695 A1* | 11/2010 | Piper .................. B01D 15/161 422/70 |
| 2012/0021407 A1 | 1/2012 | Haj-Ahmad |
| 2014/0255271 A1 | 9/2014 | Haj-Ahmad |

\* cited by examiner

METHODS AND COLUMNS FOR NUCLEIC ACID PURIFICATION

The present application is a divisional of U.S. patent application Ser. No. 14/696837 filed Apr. 27, 2015. This application is incorporated in its entirety by reference herein.

FIELD OF INVENTION

The present invention relates to methods and columns for the purification and recovery of nucleic acids, and in particular, methods and columns for the purification and recovery of high and low molecular weight RNA.

BACKGROUND

The isolation and purification of nucleic acids is a critical first step in many research and diagnostic applications. Purified nucleic acids must be of high quality, such that they can be used in sensitive downstream applications including PCR amplification, detection, sequencing, cloning and hybridization. Obtaining purified DNA or RNA is a complicated task due to the presence of large amounts of contaminating cellular materials, (e.g. proteins and carbohydrates) present in the complex environments in which the nucleic acids are found, including urine, blood, plasma, serum, saliva, feces, milk, tissues, plants, soil, yeast and fungi.

Furthermore, in addition to providing purified nucleic acids for use in downstream applications, it is also important to ensure that total nucleic acids are isolated from a sample. This is particularly important for the isolation of RNA that may be used for studies involving gene expression and gene regulation, as the quantity of a specific RNA within a cell indicates the level of expression of a particular DNA. In recent years, the study of gene expression has increased, with gene activity and nucleic acids obtained from biological samples being used to diagnose infections or diseases including cancer, and to monitor the effects of administered drugs, among other applications. Information relating to the presence and quantity of a specific RNA is critical in studying gene expression; therefore it is critical that the method of nucleic acid isolation being employed does not favour the isolation of certain sizes of RNA molecules.

Many different methods for the isolation and purification of nucleic acids have been developed over the years. Traditional methods for the isolation of nucleic acids involve the use of phenol or an organic solvent mixture containing phenol and chloroform to extract cellular materials followed by precipitation of the nucleic acids with alcohol. These traditional methods are problematic as they are time consuming (e.g. require multiple extraction steps), require the use of toxic chemicals and often provide low yields of nucleic acid. Further, the purified nucleic acids can be contaminated with the organic solvents or alcohol, both of which interfere with downstream applications.

Newer methods for the purification of nucleic acids are based on solid phase purification. With solid phase purification, the nucleic acid of interest is bound to a solid support, while impurities such as proteins and other non-target nucleic acids are washed away. The purified nucleic acid of interest is then eluted from the solid support. The first solid phase purification methods were based on the use of silica. Silica materials such as glass particles, glass powder, silica particles, glass microfibers, and diatomaceous earth have been used in combination with aqueous solutions of chaotropic salts to isolate DNA and RNA. Methods for the purification of nucleic acids using other types of support materials have also been developed, including the use of silicon carbide (SiC).

SUMMARY OF INVENTION

In one aspect, provided is a column for isolating nucleic acids, the column comprising: a housing comprising an inlet opening and an outlet opening; and a solid support disposed within the housing between the inlet and outlet openings, the solid support comprising silica and silicon carbide.

In one embodiment, the solid support comprises: a first layer and second layer, the first and second layers being in a stacked orientation; and optionally, an intermediate layer disposed between the first and second layers; wherein
 (a) the first layer comprises the silicon carbide and the second layer comprises the silica;
 (b) the first layer comprises the silica and the second layer comprises the silicon carbide, or
 (c) the first and second layers comprise the silica and the intermediate layer comprises the silicon carbide;
wherein the silicon carbide is in the form of silicon carbide particles or a slurry of silicon carbide particles, and wherein the silica is in the form of silica particles, a slurry of silica particles, one or more silica membranes, or a combination thereof. Each silica membrane can have a thickness of at least 0.5 mm.

In a further embodiment, the solid support comprises: a first layer and a second layer, the first and second layers being in a stacked orientation; and optionally, an intermediate layer disposed between the first and second layers; wherein
 (a) the first layer comprises a plurality of silica membranes, wherein the silicon carbide is deposited on a surface of at least one of the plurality of silica membranes and the second layer comprises at least one silica membrane;
 (b) the first layer comprises at least one silica membrane and the second layer comprise a plurality of silica membranes, wherein the silicon carbide is deposited on a surface of at least one of the plurality of silica membranes;
 (c) the first layer and second layer each comprise a plurality of silica membranes, wherein the silicon carbide is deposited on a surface of at least one of the plurality of silica membranes and the intermediate layer comprises at least one silica membrane; or
 (d) the first layer and second layer each comprise at least one silica membrane and the intermediate layer comprises a plurality of silica membranes, wherein the silicon carbide is deposited on a surface of at least one of the plurality of silica membranes. Each of the silica membranes can have a thickness of at least 0.5 mm.

In a further embodiment, the solid support comprises: a first layer and a second layer, the first and second layer being in stacked orientation; and optionally, an intermediate layer disposed between the first and second layers; wherein
 (a) the first layer comprises at least one silica membrane, the second layer comprise silica particles, and the intermediate layer comprises silicon carbide particles;
 (b) the first layer comprises at least one silica membrane, the second layer comprise silicon carbide particles, and the intermediate layer comprises silica particles;
 (c) the first layer comprises silicon carbide particles, the second layer comprises at least one silica membrane, and the intermediate layer comprises silica particles;
 (d) the first layer comprises silica particles, the second layer comprises at least one silica membrane, and the intermediate layer comprises silicon carbide particles;

(e) the first layer and second layer each comprise silicon carbide particles and the intermediate layer comprises silica particles; or (f) the first layer and second layer each comprise silicon carbide particles and the intermediate layer comprises at least one silica membrane. Each of the silica membranes can have a thickness of at least 0.5 mm.

In a further embodiment, the solid support comprises a mixture of silicon carbide particles and silica particles. The mixture of silica particles and silicon carbide particles can be provided in the form of a slurry.

In a further embodiment, the column is a spin column.

In another aspect, provided is a method for isolating nucleic acids from a sample containing nucleic acids, the method comprising the steps of: providing a solid support comprising silica and silicon carbide; contacting the sample with the solid support to bind the nucleic acid to the solid support; and eluting the bound nucleic acids from the solid support.

In an embodiment, the solid support comprises a mixture of silica particles and silicon carbide particles. The mixture of silica particles and silicon carbide particles can be provided as a slurry.

In a further embodiment, the solid support is provided in a column. The method can employ any of the columns described above.

The method can be used to isolate RNA or DNA. The isolated RNA or DNA can be linear or branched, single or double stranded, native, modified or synthesized, or any fragment thereof.

BRIEF DESCRIPTION OF THE DRAWINGS

Preferred embodiments of the invention will now be described, by way of example, with reference to the accompanying drawings, in which.

Figure 1:
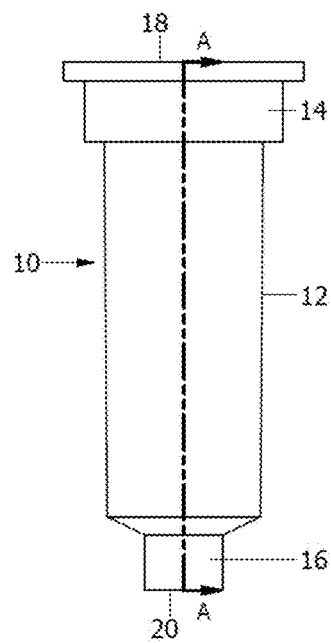
FIG. 1 is a side view of a silica/SiC hybrid column.

Similar references are used in different figures to denote similar components.

DESCRIPTION

It is known in the art that silica based purification methods tend to favour larger RNA species and does not allow for the isolation of RNA that is <200 nt in size. Therefore, when isolating total RNA using a silica based method, the user is actually isolating total RNA that is >200 nt in size. This is of particular concern for gene expression studies as the excluded small RNAs include regulatory RNA molecules, such as microRNA (miRNA) and short interfering RNA (siRNA), as well as tRNA and 5S rRNA. These small RNA molecules have attracted much attention in recent years for their role in regulating gene expression in signaling pathways, cell death, organ development and metabolism. Moreover, increasing evidence has suggested the involvement of small RNAs in human disease including cancer pathogenesis and viral-related infections.

In contrast to silica based purification methods, silicon carbide based purification methods have been shown to exhibit no size-bias when used for RNA purification. However, silicon carbide (SiC) based purification methods have been shown to have a lower capacity as compared to silica based methods for recovering RNA.

It has now been surprisingly found that using silica and SiC in combination results in an overall higher yield of nucleic acids of all sizes, including small RNAs, as compared to prior art purification methods using silica or SiC. In particular, through the use of a hybrid solid support comprising both silica and SiC, it has been surprisingly found that a higher yield of total RNA was obtained when compared to the use of solid supports consisting of silica or SiC alone. This surprising result was particularly evident in the increased amount of small RNA that was recovered using the hybrid solid support as compared to the amount of small RNA recovered using SiC alone. This was an unexpected result as it is known that silica does not isolate the small RNA molecules; therefore the use of silica and SiC together would not be expected to recover greater amounts of small RNA (e.g. <200 nt) than the use of SiC alone.

Silica/SiC Solid Supports and Columns

In one embodiment, disclosed is a solid support for the isolation and purification of nucleic acids, the solid support comprising silica and SiC. As used herein, the term "nucleic acids" refers to RNA or DNA that is linear or branched; single or double stranded; native, modified or synthesized; or any fragment thereof.

The solid support can be prepared using different types of silica materials, including, but not limited to: glass particles, glass powder, silica particles, glass microfibers, diatomaceous earth, silica sand, silica gel and mixtures thereof. Further, the solid support can be prepared using silica materials in various forms. The silica materials can be used in a slurry or bead-based format. In other embodiments, the silica materials may be formed or incorporated into structures, such as silica membranes, silica impregnated or coated filters, and silica coated magnetic beads.

The solid support can be prepared using the typical industrial preparation of SiC, which is composed of about 97.8% silicon carbide and small amounts of silicon dioxide, silicon, iron, aluminum and carbon. SiC is available in a variety of grit sizes or grades, with each grade having a different average particle size. While the solid support may be prepared using any grade of SiC, a preferred grit size is 2500. The SiC can be used in a slurry format. In other embodiments, the SiC can be applied directly onto to the silica materials. For example, SiC particles can be applied to a surface of a silica membrane by spraying.

In one embodiment, the solid support can comprise a mixture of silica particles and SiC particles provided in a slurry format. The slurry can be made in an appropriate liquid containing both the silica particles and SiC particles. The silica particles and SiC particles can be mixed in various different ratios, with a preferred ratio being a 1:1 weight ratio. In use, the slurry can be combined with an aqueous solution containing nucleic acids. The slurry is thoroughly mixed with the aqueous solution to allow the nucleic acids to bind to the silica particles and SiC particles. The solid support with the bound nucleic acids can then be separated from the liquid phase through pelleting by centrifugation, or by passing the silica particles and the SiC particles through a solid support column or through gravity settling. Once the bound particles have been separated, the nucleic acids can be eluted from the silica particles and the SiC particles using an appropriate elution solution.

In another embodiment, the solid support can be provided within a chromatography column to provide a hybrid silica/SiC column. The column may be any size, from small spin columns all the way to large chromatography columns operating through the use of gravity or pumps. In use, an aqueous solution comprising the nucleic acids to be isolated can be introduced into the column. As the sample travels through the column, the nucleic acids will come into contact to the solid support and selectively bind to the silica and SiC. The bound nucleic acids can be eluted from the solid support using an appropriate elution solution and collected for downstream applications.

In a further embodiment, the solid support is provided in a spin column, for example, spin column 10 as shown in FIG. 1. The spin column 10 can comprise an elongated housing 12 having an upper portion 14 and a lower portion 16. An inlet opening 18 is defined in the upper portion 14 of the housing 12 and is configured to receive a sample containing nucleic acids. An outlet opening 20 is defined in the lower portion 16 of the housing 12 and is configured to allow effluent and eluted nucleic acids to exit the housing. The silica materials and SiC particles comprising the solid support may be arranged in various configurations within the column housing.

In one embodiment, the solid support can be comprised of one or more layers comprising silica and one or more layers comprising SiC. The silica comprising layers and SiC comprising layers can be arranged in the column in any configuration, including in an alternating stacked fashion. The layers may be spaced apart from one another through the inclusion of other solid support media and/or one or more column fittings such as O-rings, filters, and frits. The SiC comprising layers can include SiC particles or a slurry of SiC particles. The silica comprising layers can comprise silica particles, a slurry of silica particles, one or more silica membranes, or a combination thereof.

Figure 2:
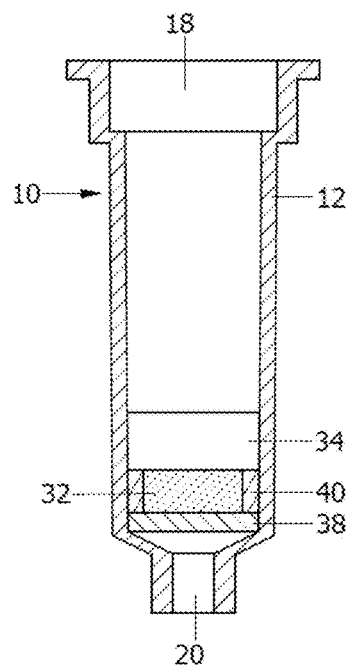
FIG. 2 is a cross-sectional view (along line A-A as shown in FIG. 1) of a first preferred embodiment of a hybrid silica/SiC column comprising a single silica comprising layer (Hybrid A).
Figure 3:
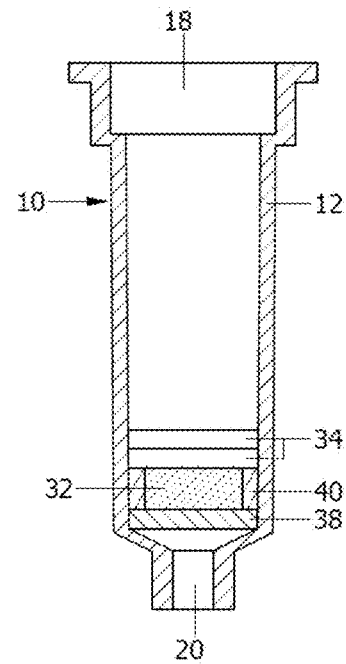
FIG. 3 is a cross-sectional view (along line A-A as shown in FIG. 1) of a first preferred embodiment of a hybrid silica/SiC column comprising a plurality of silica comprising layers (Hybrid B).

In a first preferred embodiment, as seen in FIGS. 2 and 3 (Hybrid A and B), the hybrid silica/SiC column 10 comprises a solid support comprising a first layer 32 and a second layer 34. The first and second layers 32, 34 have a stacked arrangement when the column 10 is in a vertical orientation as shown in FIGS. 2 and 3. The first layer 32 comprises the SiC and the second layer 34 comprises the silica material. It will be appreciated that the first layer 32 may be composed of varying amounts of SiC depending on the size of the column. The second layer 34 may be composed of multiple layers of silica material.

Figure 4:
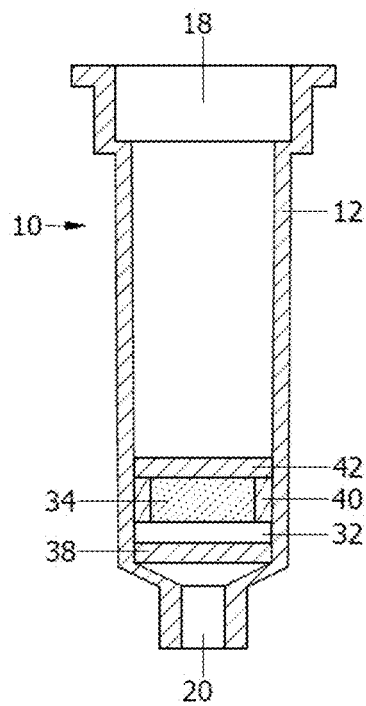
FIG. 4 is a cross-sectional view (along line A-A as shown in FIG. 1) of a second preferred embodiment of a hybrid silica/SiC column.

In a second preferred embodiment, as seen in FIG. 4, the hybrid silica/SiC column 10 comprises a solid support comprising a first layer 32 and a second layer 34. The first and second layers 32, 34 have a stacked arrangement when the column 10 is in a vertical orientation as shown in FIG. 4. The first layer 32 comprises the silica materials and the second layer 34 comprises the SiC. It will be appreciated that the first layer 32 may be composed of multiple layers of silica materials. The second layer 34 may be composed of varying amounts of SiC depending on the size of the column.

Figure 5:
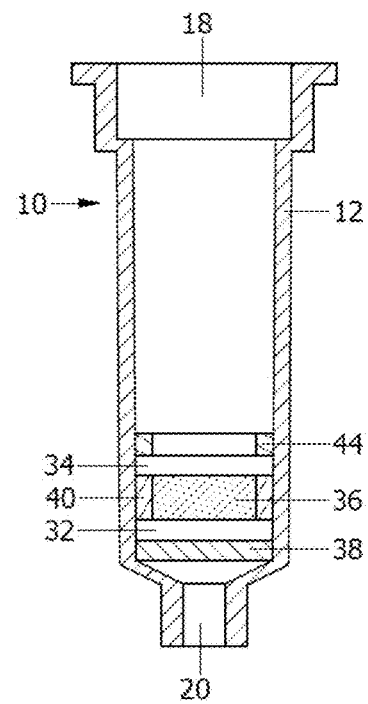
FIG. 5 is a cross-sectional view (along line A-A as shown in FIG. 1) of a third preferred embodiment of a hybrid silica/SiC column (Hybrid C) with a bottom frit.

The solid support may further comprise an intermediate layer 36 disposed between the first and second layers 32, 34. FIGS. 5 (Hybrid A) and 6 illustrate a third preferred embodiment of a hybrid silica/SiC column. The solid support comprises a first layer 32, a second layer 34 and an intermediate layer 36 disposed between the first and second layers 32, 34. In a third preferred embodiment, the first layer 32 and the second layer 34 each comprise the silica material and the intermediate layer 36 comprises the SiC. It will be appreciated that each of the first and second layers 32, 34 may be composed of multiple layers of silica material. The intermediate layer 36 may be composed of varying amounts of SiC depending on the size of the column.

It will be appreciated that the solid support may combine the silica material and SiC in different forms and different arrangements. For example, in one embodiment, the first layer can comprise at least one silica membrane, the second layer can comprise silica particles, and the intermediate layer comprises SiC particles. In another embodiment, the first layer can comprise at least one silica membrane, the second layer can comprise SiC particles, and the intermediate layer can comprise silica particles. In another embodiment, the first layer can comprise SiC particles, the second layer can comprise at least one silica membrane, and the intermediate layer can comprise silica particles. In another embodiment, the first layer can comprise silica particles, the second layer can comprises at least one silica membrane, and the intermediate layer can comprises SiC particles. In another embodiment, the first layer and second layer each can comprise SiC particles and the intermediate layer comprises silica particles. In another embodiment, the first layer and second layer each can comprise SiC particles and the intermediate layer comprises at least one silica membrane.

In the layered embodiments described herein, each of the silica comprising layers may be comprised of silica particles, a slurry of silica particles, one or more silica membranes or any combination thereof. In embodiments where the silica comprising layer is comprised of a plurality of silica membranes (e.g. the silica membranes being in a stacked arrangement), each of the silica membranes may be of varying thickness. The thickness of each silica membrane is preferably at least 0.5 mm. In some embodiments, the silica membrane may have a thickness greater than 0.5 mm, including thicknesses of 1 mm and 3 mm. It will be appreciated that each of the silica comprising layers may comprise different numbers of silica membranes and the silica membranes may be of different thicknesses. Further in these layered embodiments, the SiC comprising layers may be comprised of SiC particles or a slurry of SiC particles. It will be appreciated that different amounts and different grit sizes of SiC particles can be used in combination with the one or more silica comprising layers to provide the solid support.

To prepare a hybrid silica/SiC column comprising a solid support having a layered arrangement, the silica materials and SiC can be packed sequentially into a chromatography column, and more preferably a conventional spin column. The spin column may have a volume of about 1.0 ml and more preferably, of about 0.9 ml. The amount of SiC particles packed into the spin column is preferably about 100 mg. However, larger and smaller amounts of SiC can also be used depending on the size of the column. Depending on the arrangement of the silica comprising layer (or layers) and the choice of silica materials (e.g. use of silica particles versus silica membranes), the column can be fitted with an appropriate bottom frit material (such as for example, filter membranes from Porex, Fairburn, USA or Whatman filter papers from Sigma-Aldrich, St. Louis, USA) to prevent the loss of the support materials out the bottom of the column. In some embodiments, the column may further be provided with a top frit material (such as for example, filter membranes from Porex, Fairburn, USA or Whatman filter papers from Sigma-Aldrich, St. Louis, USA). The column may further be provided with top and/or bottom O-rings to prevent the silica comprising layers and SiC comprising layers from shifting within the column. O-rings can also be included to prevent liquid from channelling along the inner wall of the spin column.

As seen in FIGS. 2 (Hybrid A) and 3 (Hybrid B), a first preferred embodiment of the hybrid silica/SiC column 10 can be prepared by placing a bottom frit material 38, followed by a bottom O-ring 40, into a conventional spin column housing 12. The first layer 32 of the solid support is formed by placing SiC particles over the bottom frit material 38. The second layer 34 of the solid support is formed by placing at least one silica comprising layer (as shown in FIG. 2) or a plurality of silica comprising layers (as shown in FIG. 3) over the SiC particles. The second layer 34 can optionally be covered with a top frit material or a top O-ring.

As seen in FIG. 4, a second preferred embodiment of the hybrid silica/SiC column 10 can be prepared by placing a bottom frit material 38 into a conventional spin column housing 12. The first layer 32 of the solid support is formed by placing at least one silica comprising layer over bottom frit material 38. The second layer 34 of the solid support is then formed by placing SiC particles over the silica comprising layer. As seen in FIG. 4, the SiC particles can be contained within a bottom O-ring 40. A top frit material 42 can then be placed over the SiC particles.

As seen in FIG. 5 (Hybrid C), a third preferred embodiment of the hybrid silica/SiC column 10 can be prepared by placing a bottom frit material 38 into a conventional spin column housing 12. The first layer 32 is formed by placing at least one silica comprising layer over the bottom frit material 38. The intermediate layer 36 is formed by placing SiC particles on top of the silica comprising layer. As seen in FIG. 5, the SiC particles can be contained within a bottom O-ring 40. The second layer 34 is formed by placing at least one upper silica comprising layer over the SiC particles. The second layer 34 can be covered with top O-ring 44 or a top frit material 42 (not shown).

Figure 6:
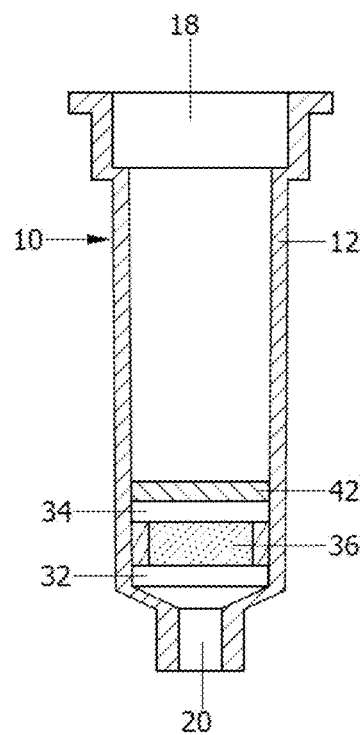
FIG. 6 is a cross-sectional view (along line A-A as shown in FIG. 1) of a third preferred embodiment of a hybrid silica/SiC column with a top frit.

As seen in FIG. 6, a third preferred embodiment of the hybrid silica/SiC column 10 can be prepared using at least one lower silica comprising layer in the form of a silica membrane as the first layer 32. In this embodiment, no bottom frit is required. Next, the SiC particles can be placed on top of the silica comprising layer to form the intermediate layer 36. As seen in FIG. 6, the SiC particles can be contained within a bottom O-ring 40. The second layer 34 is formed by placing at least one upper silica comprising layer over the SiC particles. The second layer 34 can be covered with a top frit material 42.

In a fourth preferred embodiment, the hybrid silica/SiC column can comprise a solid support comprising one or more silica membranes having SiC deposited on a surface of each of the silica membranes. The SiC treated silica membrane can be prepared by spraying at least one surface of the silica membrane with a slurry of SiC particles, and more preferably, SiC particles having a grit size of 2500. The SiC slurry used to treat the silica membrane can be about 5% to 100% w/w. The silica membranes can be sprayed with different amounts of SiC. The SiC treated silica membranes may comprise about 0.1 mg to about 10 mg of SiC per $mm^2$, more preferably about 0.5 mg to about 5 mg per $mm^2$, and more even preferably, about 0.7 mg to about 3 mg per $mm^2$. The SiC treated silica membranes can be of varying thickness, and are preferably at least 0.5 mm thick.

The hybrid silica/SiC column can be prepared by placing a bottom frit material into a conventional spin column, followed by two SiC treated silica membranes, stacked on top of one another, such that the SiC treated surfaces of the silica membranes are facing towards the inside of the stack and the untreated surfaces of the silica membranes are facing outward. In further embodiments, the stacked SiC treated silica membranes can be combined with one or more silica comprising layers. The silica comprising layers may be comprised of silica particles, a slurry of silica particles, or one or more silica membranes or a combination thereof. In embodiments where the silica comprising layer is comprised of a plurality of silica membranes, each of the silica membranes may be of varying thickness. The thickness of each silica membrane is preferably at least 0.5 mm. It will be appreciated that each of silica comprising layers may comprise different numbers of silica membranes and the silica membranes may be of different thicknesses.

Figure 7:
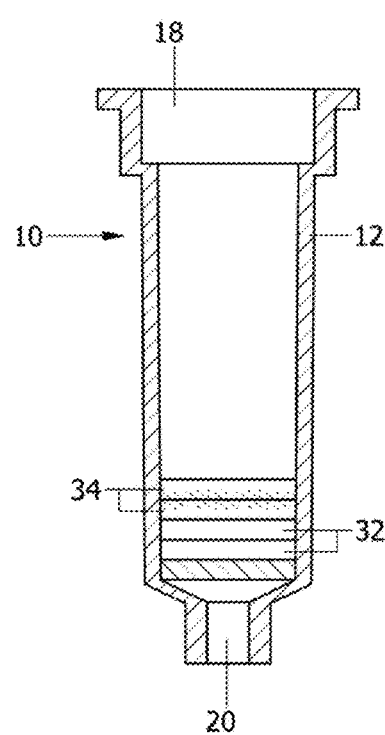
FIG. 7 is a cross-sectional view (along line A-A as shown in FIG. 1) of a fourth preferred embodiment of a hybrid silica/SiC column (Hybrid D).

The stacked SiC treated silica membranes and the one or more silica comprising layers can be arranged in any number of different configurations within the column, including in an alternating stacked orientation and in a sandwiched configuration. For example, in one embodiment, the hybrid silica/SiC column can comprise a solid support comprising a first layer 32 and a second layer 34 as shown in FIG. 7 (Hybrid D). The first and second layers are in a stacked arrangement when the column is vertically oriented along its longitudinal axis. The first layer 32 can be composed of at least one silica comprising layer and the second layer 34 can be composed of the stacked SiC treated silica membranes. In another embodiment, the first layer can be composed of the stacked SiC treated silica membranes and the second layer can be composed of at least one silica comprising layer.

In a further embodiment, the hybrid silica/SiC column can comprise a solid support comprising a first layer and a second layer and an intermediate layer disposed between the first and second layers. The first layer, intermediate layer and second layer having a stacked arrangement when the column is vertically oriented relative to its longitudinal axis. Each of the first and second layers can be composed of at least one silica comprising layer. The intermediate layer can be composed of the stacked SiC treated silica membranes. In another embodiment, each of the first and second layers can be composed of stacked SiC treated silica membranes and the intermediate layer can be composed of at least one silica comprising layer.

In a fifth preferred embodiment, the hybrid silica/SiC column comprises a solid support comprising silica particles and SiC particles packed into a conventional spin column. The hybrid silica/SiC column can be prepared using a slurry of SiC particles and liquid (1:1 ratio by weight) and an slurry of silica particles and liquid (1:1 ratio by weight). In one embodiment, the hybrid silica/SiC column is prepared by first placing a bottom frit into the column, followed by 50% by weight SiC particles and then topped with 50% by weight silica particles for a total of 100 mg of resin in the column. A top frit material is then placed on top of the packed resins. In another embodiment, the hybrid silica/SiC column is prepared by first placing a bottom frit into the column, followed by 50% silica particle, and then topped with 50% SiC for a total of 100 mg of resin in the column. A top frit material is then placed on top of the packed resins. The hybrid silica/SiC columns can be prepared using any grade of SiC, with a preferred grit size being 2500. A preferred particle size for the silica particles is at least 2 microns. It will be appreciated that the hybrid silica/SiC columns can be prepared using different ratios of SiC particles: silica particles, and can also be made by adding at least one silica comprising layer (as described above) above and/or below the packed resins in the column.

In a sixth preferred embodiment, the hybrid silica/SiC column comprises a solid support comprising a mixture of silica particles and SiC particles. The mixture can be formed using the silica particles and the SiC particles as described above. A slurry can be made in an appropriate liquid which contains both SiC particles and silica particles. The SiC and silica particles can be mixed in different ratios. The slurry mixture can then be packed into a conventional spin column fitted with a bottom frit, and a top frit can be placed on top of the combined SiC and silica slurry mixture. In another embodiment, the slurry can be packed into a column by stabilizing the slurry using any supporting matrix known in the art, including gel and polymer matrices. In another preferred embodiment these hybrid columns made with a mixture of SiC and silica particles can also contain additional layers of silica membrane either above the hybrid resin, below the hybrid resin, or both above and below the hybrid resin.

Methods for the Isolation and Purification of Nucleic Acids

In another embodiment, disclosed is a method for isolating nucleic acids from a sample containing nucleic acids. The method can comprise the steps of: providing a solid support comprising silica and silicon carbide; contacting the sample with the solid support to bind the nucleic acid to the solid support; and eluting the bound nucleic acids from the solid support.

The method can be used to isolate nucleic acids from different types of biological samples, including but not limited to blood, saliva, plasma, serum, urine, sputum, stool, cerebral spinal fluid, cells, tissues, plants, fungi, bacteria and virus. The biological samples can be prepared using conventional homogenization and lysis methods (as appropriate to the sample type) to provide an aqueous solution containing the nucleic acids to be recovered and which is substantially free of cellular debris. Exemplary methods for the preparation of tissue and cells samples are set out in the Examples section below. The disclosed method can also be used to isolate nucleic acids from solutions including enzymatic reactions, melted gel slices, or any other nucleic acid-containing solution.

The method can be carried out using any of the solid supports described above. In one embodiment, the solid support can comprise a slurry of silica particles and SiC particles, preferably in a 1:1 ratio by weight. The slurry mixture can be added to an aqueous solution containing nucleic acids (for example, a lysate solution mixed with a suitable amount of ethanol). The slurry is thoroughly mixed with the aqueous solution to allow the nucleic acids to bind to the silica particles and SiC particles under low salt conditions and slightly acidic to neutral pH conditions of about pH 4-7. The solid support with the bound nucleic acids can then be separated from the liquid phase through pelleting by centrifugation, or by passing the silica particles and the SiC particles through a solid support column or through gravity settling. Once the bound particles have been separated, the nucleic acids can be eluted from the silica particles and the SiC particles using an appropriate low salt elution solution (for example, 1-10 mM Tris.HCl) under slightly basic to neutral pH conditions of about pH 7-9 and collected for downstream applications.

In another embodiment, the method can be carried out using any of the hybrid silica/SiC columns described above. In a preferred embodiment, the method is carried out using a hybrid silica/SiC spin column and conventional spin column methodology for recovering the nucleic acids. For example, an aqueous solution containing nucleic acids (for example, a lysate solution mixed with a suitable amount of ethanol) can be loaded into the spin column using a pipette. The spin column is centrifuged causing the sample to travel through the spin column. The nucleic acids contained in the sample will come into contact to the solid support and selectively bind to the silica and SiC under slightly acidic to neutral pH conditions of about pH 4-7. The resulting column flow-through can be discarded. The spin column can then be washed with an appropriate low salt wash solution (for example, 1-100 mM Tris.HCl, MOPS or HEPES with 0-100 mM NaCl or KCl) to remove materials not selectively bound to the solid support. The bound nucleic acids can then be eluted from the solid support using an appropriate low salt elution solution (for example, 1-10 mM Tris.HCl) under slightly basic to neutral pH conditions of about pH 7-9 and collected for downstream applications.

EXAMPLES

Example 1

A hybrid column (Hybrid C Having the Solid Support arrangement shown in FIG. 5) was tested for its ability to isolate total RNA from HeLa cell lysate, and the performance was compared to control columns of SiC alone and silica alone. The hybrid column contain a bottom frit, followed by a single layer of 1 mm silica membrane, 95 mg of silicon carbide resin grit size 2500, and another single layer of 1 mm silica membrane on top of the SiC resin. The control silica columns contained 4 sheets of silica membrane with a thickness of 1 mm each, and the control SiC column contained a bottom frit, 95 mg of 100% SiC slurry with a grit size of 2500, followed by a top frit.

One large confluent plate of HeLa cells was used for the input, and 9.1 mL of the Lysis Solution from Norgen's Total RNA Purification Kit (Cat#17200, Norgen, Thorold, Canada) was added to the cells and it was vortexed to mix. Next, 5.2 mL of ethanol was added, and again it was vortexed to mix. Next, 550 µL of the lysate was applied to each of the columns (3×Hybrid C, 3×Silica Control, 3×SiC control). The columns were centrifuged for 1 minute at 14,000 rpm for binding of the nucleic acids. Next, 400 µL of Wash Solution from Norgen's Total RNA Purification Kit (Cat#17200, Norgen, Thorold, Canada) was added to each column, and the columns were spun at 14,000 rpm for 1 minute. The wash step was repeated two more times for a total of 3 washes. The columns were then spun empty for 2 minutes at 14,000 rpm in order to dry the columns. Lastly, the bound total RNA was eluted from the columns using 50 µL of the Elution Solution from the Total RNA Purification Kit (Cat#17200, Norgen, Thorold, Canada).

Figure 8:
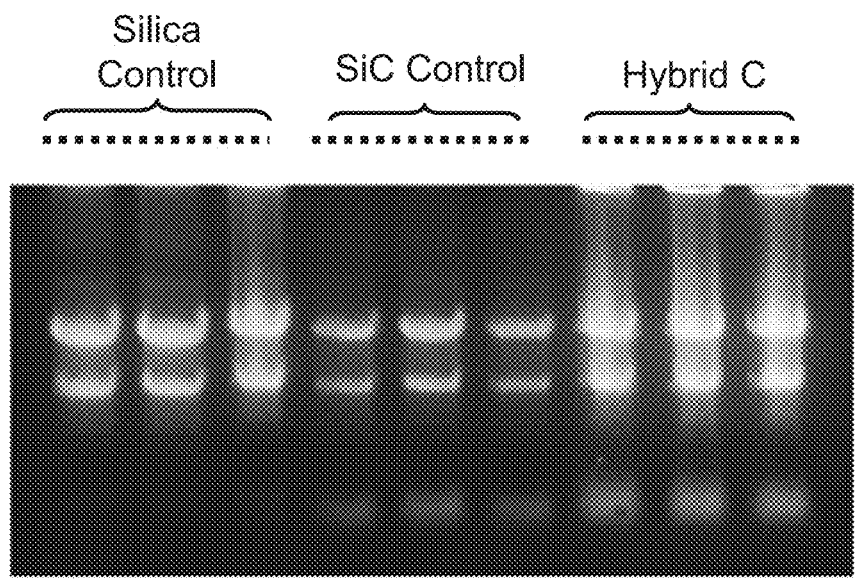
FIG. 8 is a gel image showing the resolution of RNA that is isolated from HeLa cells using a silica/SiC hybrid column (Hybrid C) and control SiC columns and control silica columns.

For visual analysis, 5 µL of each of the elutions was run on a 1×MOPS, 1.5% formaldehyde-agarose gel (150V for 30 minutes). The gel image can be seen in FIG. 8, indicating that the total RNA profile could be isolated using the hybrid columns, which is similar to the SiC control column (isolated both large and small RNA). Also, as seen from the gel, the overall yield of total RNA when using the hybrid column was much higher than when the SiC control column or silica control column was used.

To further analyze the yield, the RNA was quantified using a GE Nanovue Plus Nanodrop. This analysis revealed the superior performance of the hybrid column. As it can be seen in Table 1, the average yield using the hybrid column was 19.24 µg, whereas the yield using the control silica column was 8.79 µg and the yield using the control SiC column was 13.62 µg.

TABLE 1

| Column Type | Average Yield (µg) | Standard Deviation |
|---|---|---|
| Silica Control | 13.62 | 0.20 |
| SiC Control | 8.79 | 1.29 |
| Hybrid C | 19.24 | 0.50 |

Example 2

A hybrid column (Hybrid A having the solid support arrangement shown in FIG. 2) was tested for its ability to isolate total RNA from *E. coli* lysate, and the performance was compared to control columns of SiC alone. The hybrid columns were made by placing a bottom frit into a column, and then adding 95 mg of 100% SiC slurry with a grit size of 2500, followed by a single silica membrane of 3 mm thickness. The control SiC columns contained a bottom frit, 100 mg of 100% SiC slurry with a grit size of 2500, followed by a top frit.

For each isolation, 1 mL of *E. coli* culture lysate was used as the input. Initially, 20 mL of culture was spun down, and the pellet was resuspended in 2 mL of 1 mg/mL lysozyme and then incubated at room temperature for 5 minutes. Next, 7 mL of the Lysis Solution from Norgen's Total RNA Purification Kit (Cat#17200, Norgen, Thorold, Canada) was added to the lysate and it was vortexed to mix. Next, 4 mL of ethanol was added, and again it was vortexed to mix. Next, 1 mL of the lysate was applied to each of the columns (3×SiC Control, 3×Hybrid A Column). The columns were centrifuged for 1 minute at 14,000 rpm for binding of the nucleic acids. Next, 400 µL of Wash Solution from Norgen's Total RNA Purification Kit (Cat#17200, Norgen, Thorold, Canada) was added to each column, and the columns were spun at 14,000 rpm for 1 minute. The wash step was repeated two more times for a total of 3 washes. The columns were then spun empty for 2 minutes at 14,000 rpm in order to dry the columns. Lastly, the bound total RNA was eluted from the columns using 50 µL of the Elution Solution from the Total RNA Purification Kit (Cat#17200, Norgen, Thorold, Canada).

Figure 9:
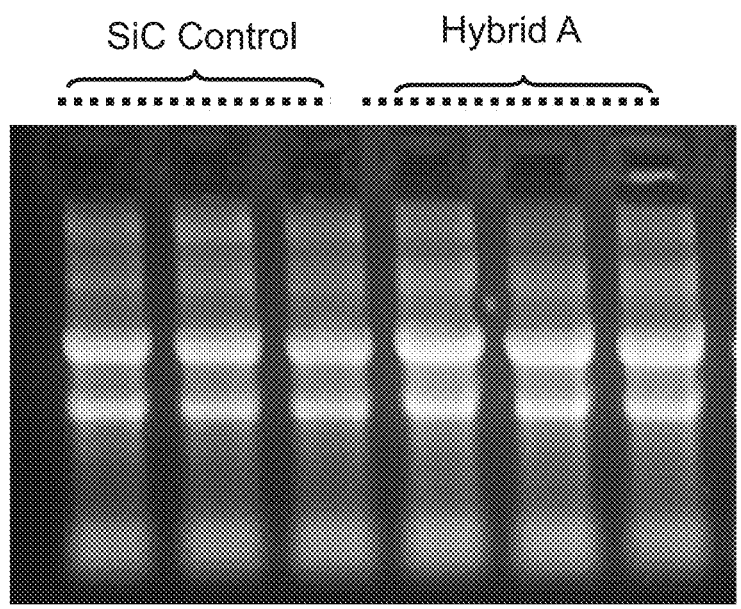
FIG. 9 is a gel image showing the resolution of RNA that is isolated from E. coli using a silica/SiC hybrid column (Hybrid A) and control SiC columns.

For visual analysis, 5 µL of each of the elutions was run on a 1×MOPS, 1.5% formaldehyde-agarose gel (150V for 30 minutes). The gel image can be seen in FIG. 9, indicating that the total RNA profile could be isolated using the hybrid columns, which is similar to the SiC control column (isolated both large and small RNA). In addition, the gel indicates that the overall yield of total RNA isolated using the hybrid column was much higher than when the SiC control column was used.

To further analyze the yield, the RNA was quantified using a GE Nanovue Plus Nanodrop. This analysis revealed the superior performance of the hybrid column. As it can be seen in Table 2, the average yield using the hybrid column was 31.0 µg, whereas the yield using the control SiC column was 21.4 µg.

TABLE 2

| Column Type | Average Yield (µg) | Standard Deviation |
|---|---|---|
| SiC Control | 21.4 | 1.4 |
| Hybrid A | 31.0 | 2.8 |

Example 3

A hybrid column (Hybrid C) having the solid support arrangement shown in FIG. 5) was tested for its ability to isolate total RNA from Hamster liver lysate, and the performance was compared to control columns of SiC alone. The hybrid column contained a bottom frit, followed by a single layer of 1 mm silica membrane, 95 mg of silicon carbide resin grit size 2500, and another single layer of 1 mm silica membrane on top of the SiC resin. The control SiC columns contained a bottom frit, 95 mg of 100% SiC slurry with a grit size of 2500, followed by a top frit.

Ten mg of Hamster liver was used for the input, and was ground into a fine powder using liquid nitrogen. To prepare the lysate 4.8 mL of the Lysis Solution from Norgen's Total RNA Purification Kit (Cat#17200, Norgen, Thorold, Canada) was added to the cells and it was vortexed to mix. Next, the lysate was spun down to pellet insoluble materials, and the supernatant was aliquoted into 300 µL aliquots. Next, 300 µL of ethanol was added, and again it was vortexed to mix. Next, 600 µL of the lysate was applied to each of the columns (3×Hybrid C, 3×SiC control). The columns were centrifuged for 1 minute at 14,000 rpm for binding of the nucleic acids. Next, 400 µL of Wash Solution from Norgen's Total RNA Purification Kit (Cat#17200, Norgen, Thorold, Canada) was added to each column, and the columns were spun at 14,000 rpm for 1 minute. The wash step was repeated two more times for a total of 3 washes. The columns were then spun empty for 2 minutes at 14,000 rpm in order to dry the columns. Lastly, the bound total RNA was eluted from the columns using 50 µL of the Elution Solution from the Total RNA Purification Kit (Cat#17200, Norgen, Thorold, Canada).

Figure 10:
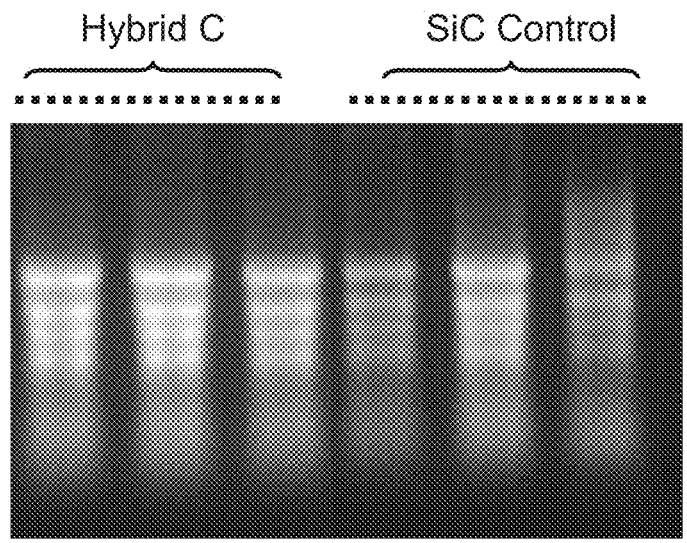
FIG. 10 is a gel image showing the resolution of RNA that is isolated from Hamster liver cells using a silica/SiC hybrid column (Hybrid C) and control SiC columns.

For visual analysis, 5 µL of each of the elutions was run on a 1×MOPS, 1.5% formaldehyde-agarose gel (150V for 30 minutes). The gel image can be seen in FIG. 10, indicating that the total RNA profile could be isolated using the hybrid columns, which is similar to the SiC control column (isolated both large and small RNA).

To further analyze the yield, the RNA was quantified using a GE Nanovue Plus Nanodrop. This analysis revealed the superior performance of the hybrid column. As it can be seen in Table 3, the average yield using the hybrid column was 44.8 µg, whereas the yield using the control SiC column was 21.2 µg.

TABLE 3

| Column Type | Average Yield (µg) | Standard Deviation |
| --- | --- | --- |
| Hybrid C | 44.8 | 1.9 |
| Control SiC | 21.2 | 7.1 |

Example 4

A different hybrid column was tested for its ability to isolate total RNA from E. coli lysate. The hybrid column (Hybrid D having the solid support arrangement shown in FIG. 7) contained silica sheets sprayed with SiC. To make these sheets, 1 mm thick silica membranes are sprayed with a 100% slurry of SiC with a grit size of 2500. The silica is sprayed in such a way that the SiC is deposited evenly on the silica membrane and not in clumps. Two such sprayed sheets are then placed together with the SiC layers facing inwards. The column is then made by placing a bottom frit into a column, then placing 2 sheets of 1 mm thick silica membrane into the column, and then placing the 2 layers of silica sheets that have been sprayed with SiC. Each of these columns contains an average of 23 mg of SiC. The control silica columns contained 4 sheets of silica membrane with a thickness of 1 mm each, and the control SiC columns contained a bottom frit, 100 mg of 100% SiC slurry with a grit size of 2500, followed by a top frit were also used.

For each isolation, 0.5 mL of E. coli culture was used as the input. Initially, 7.5 mL of culture was spun down, and the pellet was resuspended in 2 mg/mL of lysozyme and then incubated at room temperature for 5 minutes. Next, 4.5 mL of the Lysis Solution from Norgen's Total RNA Purification Kit (Cat#17200, Norgen, Thorold, Canada) was added to the lysate and it was vortexed to mix. Next, 3 mL of ethanol was added, and again it was vortexed to mix. Next, 600 µL of the lysate was applied to each of the columns (3×Hybrid D, 3×silica control, 3×SiC control). The columns were centrifuged for 1 minute at 14,000 rpm for binding of the nucleic acids. Next, the columns were washed 3 times using Wash Solution from Norgen's Total RNA Purification Kit (Cat#17200, Norgen, Thorold, Canada). The columns were then spun empty for 2 minutes at 14,000 rpm in order to dry the columns. Lastly, the bound total RNA was eluted from the columns using 50 µL of the Elution Solution from the Total RNA Purification Kit (Cat#17200, Norgen, Thorold, Canada).

Figure 11:
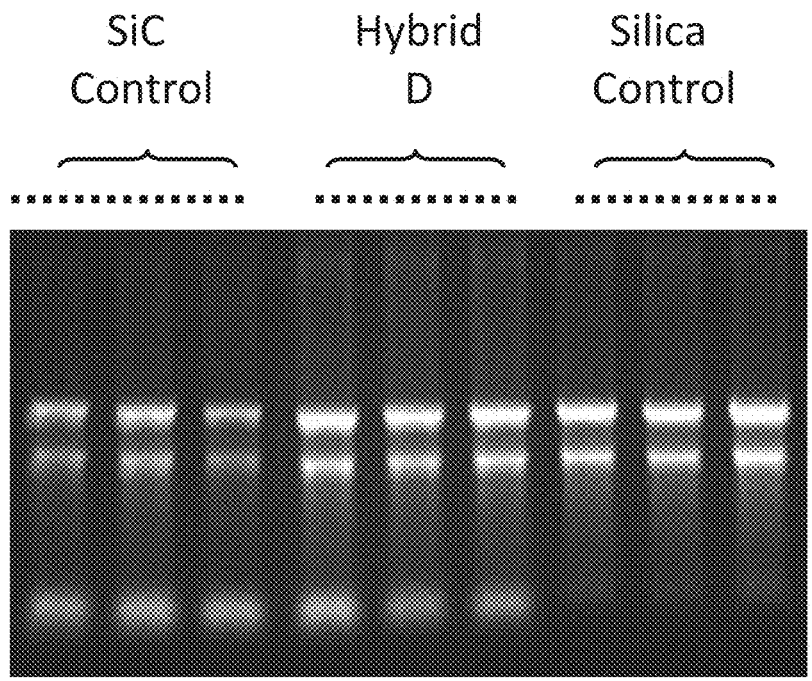
FIG. 11 is a gel image showing the resolution of RNA that is isolated from E. coli using a silica/SiC hybrid column (Hybrid D) and control SiC columns and control silica columns.

For visual analysis, 5 µL of each of the elutions was run on a 1×MOPS, 1.5% formaldehyde-agarose gel (150V for 30 minutes). The gel image can be seen in FIG. 11, indicating that the total RNA profile could be isolated using the hybrid column (isolated both large and small RNA).

To further analyze the yield, the RNA was quantified using a GE Nanovue Plus Nanodrop. This analysis revealed the superior performance of the hybrid column. As it can be seen in Table 4, the average yield using Hybrid Column D was 19.97, whereas the yield using the control silica column was 14.42 µg and the yield using the control SiC column was 13.68 µg.

TABLE 4

| Column Type | Average Yield (µg) | Standard Deviation |
| --- | --- | --- |
| SiC Control | 13.68 | 1.79 |
| Hybrid D | 19.97 | 1.26 |
| Silica Control | 14.42 | 0.36 |

Example 5

A different hybrid column was tested for its ability to isolate total RNA from HeLa cell lysate. The hybrid column contains a bottom frit, 95 mg of silicon carbide resin, and 2 layers of silica membrane with a thickness of 1 mm each on top of the SiC resin (Hybrid B having the solid support arrangement shown in FIG. 3). Control SiC columns were also used that contained a bottom frit, 95 mg of 100% SiC slurry with a grit size of 2500, followed by a top frit.

One large confluent plate of HeLa cells was used for the input, and 9.1 mL of the Lysis Solution from Norgen's Total RNA Purification Kit (Cat#17200, Norgen, Thorold, Canada) was added to the cells and it was vortexed to mix. Next, 5.2 mL of ethanol was added, and again it was vortexed to mix. Next, 550 µL of the lysate was applied to each of the columns (10×Hybrid B, 10×SiC control). The columns were centrifuged for 1 minute at 14,000 rpm for binding of the nucleic acids. Next, 400 µL of Wash Solution from Norgen's Total RNA Purification Kit (Cat#17200, Norgen, Thorold, Canada) was added to each column, and the columns were spun at 14,000 rpm for 1 minute. The wash step was repeated two more times for a total of 3 washes. The columns were then spun empty for 2 minutes at 14,000 rpm in order to dry the columns. Lastly, the bound total RNA was eluted from the columns using 50 µL of the Elution Solution from the Total RNA Purification Kit (Cat#17200, Norgen, Thorold, Canada).

Figure 12:
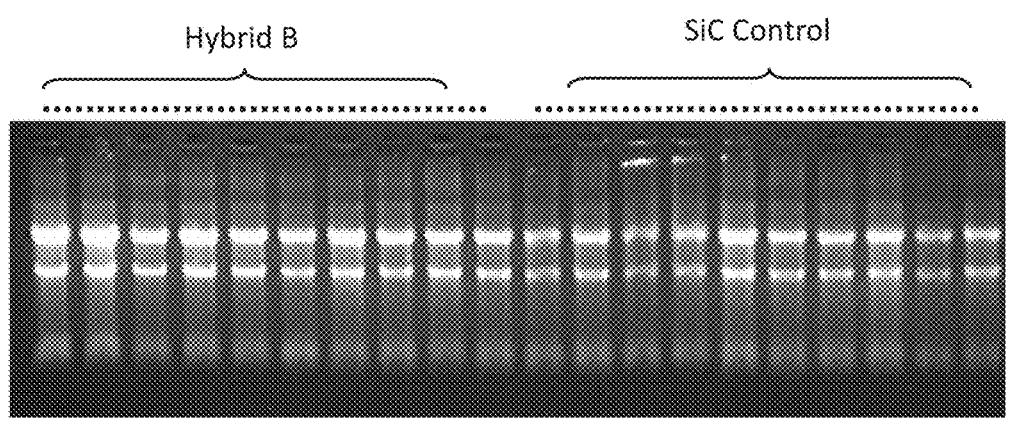
FIG. 12 is a gel image showing the resolution of RNA that is isolated from HeLa cells using a silica/SiC hybrid column (Hybrid B) and control SiC columns.

For visual analysis, 5 µL of each of the elutions was run on a 1×MOPS, 1.5% formaldehyde-agarose gel (150V for 30 minutes). The gel image can be seen in FIG. 12, indicating that the total RNA profile could be isolated using the hybrid columns, which is similar to the SiC control column (isolated both large and small RNA). Also, the overall yield of total RNA when using the hybrid column was much higher than when the SiC control column was used.

To further analyze the yield, the RNA was quantified using a GE Nanovue Plus Nanodrop. This analysis revealed the superior performance of the hybrid column. As it can be seen in Table 5, the average yield using the hybrid column was 19.7 µg, whereas the yield using the control SiC column was 14.4 µg.

TABLE 5

| Column Type | Average Yield (µg) | Standard Deviation |
| --- | --- | --- |
| Hybrid B | 19.7 | 1.8 |
| SiC Control | 14.4 | 2.4 |

Example 6

A hybrid column (Hybrid C having the solid support arrangement shown in FIG. 6) was tested for its ability to isolate total RNA from hamster liver FFPE tissue, and the performance was compared to control columns of SiC alone. The hybrid column contain a bottom frit, followed by a single layer of 1 mm silica membrane, 95 mg of silicon carbide resin grit size 2500, and another single layer of 1 mm silica membrane on top of the SiC resin. The control SiC columns contained a bottom frit, 95 mg of 100% SiC slurry with a grit size of 2500, followed by a top frit.

Two mg of unsectioned blocks of hamster liver FFPE tissue was used for the input, and were trimmed of excess paraffin. The blocks were first deparaffinized by placing the blocks into microcentrifuge tubes, and adding 1 mL of xylene to the sample. The tubes were incubated at 50° C. for 5 minutes, followed by centrifugation and removal of the xylene. Next, the samples were washed with 1 mL of ethanol and air dried at room temperature. To prepare the lysate, 300 μL of Digestion Buffer from Norgen's FFPE RNA Purification Kit (Cat#25300, Norgen, Thorold, Canada) and 10 μL of Proteinase K was to the sample, followed by incubation at 55° C. for 15 minutes and incubation at 80° C. for 15 minutes. Next, 300 μL of Binding Solution and 600 μL of ethanol was added. From this, 600 μL of the lysate was applied to each of the columns (3×Hybrid C, 3×SiC control). The columns were centrifuged for 1 minute at 14,000 rpm for binding of the nucleic acids. Next, 400 μL of Wash Solution from Norgen's FFPE RNA Purification Kit (Cat#25300 Norgen, Thorold, Canada) was added to each column, and the columns were spun at 14,000 rpm for 1 minute. The wash step was repeated two more times for a total of 3 washes. The columns were then spun empty for 2 minutes at 14,000 rpm in order to dry the columns. Lastly, the bound total RNA was eluted from the columns using 50 μL of the Elution Solution from the FFPE RNA Purification Kit (Cat#25300, Norgen, Thorold, Canada).

To analyze the yield, the RNA was quantified using a GE Nanovue Plus Nanodrop, and this analysis revealed the superior performance of the hybrid column. As it can be seen in Table 6, the average yield using the hybrid column was 5.3 μg, whereas the yield using the control SiC column was 4.2 μg.

TABLE 6

| Column Type | Average Yield (μg) | Standard Deviation |
|---|---|---|
| Hybrid C | 5.3 | 0.2 |
| SiC Control | 4.2 | 0.5 |

To further analyze the performance of the hybrid column, the purified RNA was used in RT-qPCR reactions for the detection of both large RNA and microRNA. Briefly, for the reverse transcription 1 μg of the purified RNA was used in a 20 μL reaction using Invitrogens Superscript III System to generate the cDNA. Next, 3 μL of the cDNA was used in a 20 μL SYBER Green qPCR reaction with specific primers for β-actin (large RNA) and miR-30b and miR-21 (microRNAs). The following PCR program was then run for 40 cycles:
- 95° C. for 15 seconds
- 60° C. for 30 seconds
- 72° C. for 45 seconds The Ct values from the RT-qPCR reactions were then analyzed, and the results can be seen in Table 7. It was found that for the β-actin (large RNA) and both miR-30b and miR-21 (small RNAs) the Ct values obtained from the hybrid column were lower than the Ct values obtained from the control SiC column. A lower Ct number indicates a higher starting amount of RNA. These results indicate that the increase in total RNA recovery involves an increase in the recovery of all sizes of RNA. The increase in yield of small RNA when using the hybrid column when compared to the SiC control is not expected, as it is known that silica is not able to isolate small RNA molecules such as microRNA. Therefore, when using a combination of silica and SiC, it would not be expected that higher levels of microRNA would be isolated than when using SiC alone. These results clearly indicate the hybrid column provides an unexpected effect of higher yields of total RNA, and in particular small RNA, when silica and SiC are used together.

TABLE 7

| Column Type | B-actin Ct Value | | miR-30b Ct Value | | miR-21 Ct Value | |
|---|---|---|---|---|---|---|
| | Average | Standard Deviation | Average | Standard Deviation | Average | Standard Deviation |
| Hybrid C | 24.4 | 0.0 | 19.6 | 0.8 | 14.1 | 1.1 |
| SiC Control | 25.2 | 0.1 | 21.4 | 0.1 | 18.9 | 0.3 |

The invention claimed is:

1. A column for isolating nucleic acids, the column comprising:
   a housing comprising an inlet opening and an outlet opening; and
   a solid support disposed within the housing between the inlet and outlet openings, the solid support comprising silica and silicon carbide, wherein:
   (a) the solid support comprises a plurality of layers, each of the layers comprising the silica, the silicon carbide or a combination thereof and wherein at least two layers are different; or
   (b) the solid support comprises a mixture of the silica and the silicon carbide in an approximately 1:1 weight ratio.

2. The column of claim 1, wherein the solid support comprises:
   a first layer and second layer, the first and second layers being in a stacked orientation; and optionally, an intermediate layer disposed between the first and second layers;
   wherein
   (a) the first layer comprises the silicon carbide and the second layer comprises the silica;
   (b) the first layer comprises the silica and the second layer comprises the silicon carbide; or
   (c) the first and second layers comprise the silica and the intermediate layer comprises the silicon carbide;
   wherein the silicon carbide is in the form of silicon carbide particles or a slurry of silicon carbide particles, and
   wherein the silica is in the form of silica particles, a slurry of silica particles, one or more silica membranes, or a combination thereof.

3. The column of claim 2, wherein the silica is in the form of one or more silica membranes and each silica membrane has a thickness of at least 0.5 mm.

4. The column of claim 1, wherein the solid support comprises:
   a first layer and a second layer, the first and second layers being in a stacked orientation; and optionally, an intermediate layer disposed between the first and second layers;
   wherein
   (a) the first layer comprises a plurality of silica membranes, wherein the silicon carbide is deposited on a surface of at least one of the plurality of silica membranes and the second layer comprises at least one silica membrane;

(b) the first layer comprises at least one silica membrane and the second layer comprise a plurality of silica membranes, wherein the silicon carbide is deposited on a surface of at least one of the plurality of silica membranes;

(c) the first layer and second layer each comprise a plurality of silica membranes, wherein the silicon carbide is deposited on a surface of at least one of the plurality of silica membranes and the intermediate layer comprises at least one silica membrane; or (d) the first layer and second layer each comprise at least one silica membrane and the intermediate layer comprises a plurality of silica membranes, wherein the silicon carbide is deposited on a surface of at least one of the plurality of silica membranes.

5. The column of claim 4, wherein each silica membrane has a thickness of at least 0.5 mm.

6. The column of claim 1, wherein the solid support comprises:

a first layer and a second layer, the first and second layer being in stacked orientation; and an intermediate layer disposed between the first and second layers;

wherein (a) the first layer comprises at least one silica membrane, the second layer comprise silica particles, and the intermediate layer comprises silicon carbide particles;

(b) the first layer comprises at least one silica membrane, the second layer comprise silicon carbide particles, and the intermediate layer comprises silica particles;

(c) the first layer comprises silicon carbide particles, the second layer comprises at least one silica membrane, and the intermediate layer comprises silica particles;

(d) the first layer comprises silica particles, the second layer comprises at least one silica membrane, and the intermediate layer comprises silicon carbide particles;

(e) the first layer and second layer each comprise silicon carbide particles and the intermediate layer comprises silica particles; or (f) the first layer and second layer each comprise silicon carbide particles and the intermediate layer comprises at least one silica membrane.

7. The column of claim 6,
wherein the first layer comprises at least one silica membrane, the second layer comprise silica particles, and the intermediate layer comprises silicon carbide particles; and
wherein the at least one silica membrane has a thickness of at least 0.5 mm.

8. The column of claim 6,
wherein the first layer comprises at least one silica membrane, the second layer comprise silicon carbide particles, and the intermediate layer comprises silica particles; and
wherein the at least one silica membrane has a thickness of at least 0.5 mm.

9. The column of claim 6,
wherein the first layer comprises silicon carbide particles, the second layer comprises at least one silica membrane, and the intermediate layer comprises silica particles; and
wherein the at least one silica membrane has a thickness of at least 0.5 mm.

10. The column of claim 6,
wherein the first layer comprises silica particles, the second layer comprises at least one silica membrane, and the intermediate layer comprises silicon carbide particles; and
wherein the at least one silica membrane has a thickness of at least 0.5 mm.

11. The column of claim 6,
wherein the first layer and second layer each comprise silicon carbide particles and the intermediate layer comprises at least one silica membrane; and
wherein the at least one silica membrane has a thickness of at least 0.5 mm.

12. The column of claim 1, wherein the mixture is a mixture of silicon carbide particles and silica particles.

13. The column of claim 12, wherein the mixture of silica particles and silicon carbide particles is in the form of a slurry.

14. The column of claim 1, wherein the column is a spin column.

* * * * *